(12) United States Patent
Moradian et al.

(10) Patent No.: US 8,591,577 B2
(45) Date of Patent: Nov. 26, 2013

(54) CAPSULOTOMY DEVICE AND METHOD USING ELECTROMAGNETIC INDUCTION HEATING

(75) Inventors: Ala Moradian, St. Louis, MO (US); Joseph Gruber, Maryland Heights, MO (US)

(73) Assignee: Bausch & Lomb Incorporated, Rochester, NY (US)

( * ) Notice: Subject to any disclaimer, the term of this patent is extended or adjusted under 35 U.S.C. 154(b) by 43 days.

(21) Appl. No.: 12/969,663

(22) Filed: Dec. 16, 2010

(65) Prior Publication Data

US 2012/0158130 A1 Jun. 21, 2012

(51) Int. Cl.
*A61F 2/14* (2006.01)
(52) U.S. Cl.
USPC .............................................. 623/4.1; 606/45
(58) Field of Classification Search
USPC ........................ 606/27–52; 623/4.1
See application file for complete search history.

(56) References Cited

U.S. PATENT DOCUMENTS

| | | |
|---|---|---|
| 4,570,632 A | 2/1986 | Woods |
| 4,708,138 A | 11/1987 | Pazandak |
| 4,766,896 A | 8/1988 | Pao |
| 4,805,616 A | 2/1989 | Pao |
| 4,911,161 A | 3/1990 | Schechter |
| 5,167,618 A | 12/1992 | Kershner |
| 5,266,764 A | 11/1993 | Fox et al. |
| 5,269,787 A | 12/1993 | Cozean, Jr. et al. |
| 5,312,413 A | 5/1994 | Eaton et al. |
| 5,342,377 A | 8/1994 | Lazerson |
| 5,346,491 A | 9/1994 | Oertli |
| 5,360,398 A | 11/1994 | Grieshaber et al. |
| 5,366,443 A | 11/1994 | Eggers et al. |
| 5,370,652 A | 12/1994 | Kellan |
| 5,411,510 A | 5/1995 | Fugo |
| 5,441,503 A | 8/1995 | Considine et al. |
| 5,573,533 A | 11/1996 | Strul |
| 5,669,923 A | 9/1997 | Gordon |
| 5,683,592 A | 11/1997 | Bartholomew et al. |
| 5,720,745 A | 2/1998 | Farin et al. |
| 5,728,117 A | 3/1998 | Lash |
| 5,817,092 A | 10/1998 | Behl |
| 5,860,994 A | 1/1999 | Yaacobi |
| 5,921,999 A | 7/1999 | Dileo |
| 5,957,921 A | 9/1999 | Mirhashemi et al. |
| 6,066,138 A | 5/2000 | Sheffer et al. |

(Continued)

FOREIGN PATENT DOCUMENTS

| | | |
|---|---|---|
| EP | 1809196 | 10/2005 |
| ES | 2 103 635 A1 | 9/1997 |

(Continued)

OTHER PUBLICATIONS

International Search Report (PCTISA/210)and Written Opinion (PCT/ISA/237) mailed on Feb. 20, 2012.

(Continued)

*Primary Examiner* — William H. Matthews
(74) *Attorney, Agent, or Firm* — Michael L. Smith

(57) ABSTRACT

A capsulotomy device for use in an eye having a capsular bag, comprising a conductive, primary coil capable of generating magnetic field lines and a conductive, secondary coil configured to permit insertion through an incision having a diameter of 3 mm or less, and placement on the capsular bag. When the magnetic field lines are projected through the secondary coil, a current is generated within the secondary coil.

8 Claims, 4 Drawing Sheets

(56) References Cited

U.S. PATENT DOCUMENTS

| | | |
|---|---|---|
| 6,086,583 A | 7/2000 | Ouchi |
| 6,142,996 A | 11/2000 | Mirhashemi et al. |
| 6,165,190 A | 12/2000 | Nguyen |
| D436,662 S | 1/2001 | Chandler et al. |
| D436,663 S | 1/2001 | Chandler et al. |
| D437,413 S | 2/2001 | Chandler et al. |
| 6,229,127 B1 | 5/2001 | Link |
| 6,306,155 B1 | 10/2001 | Chandler et al. |
| 6,551,326 B1 | 4/2003 | Van Heugten et al. |
| 6,592,541 B1 | 7/2003 | Kurwa |
| 6,629,980 B1 | 10/2003 | Eibschitz-Tsimhoni |
| 6,670,590 B1 | 12/2003 | Pacholok et al. |
| 6,676,658 B2 | 1/2004 | Burban et al. |
| 6,780,178 B2 | 8/2004 | Palanker et al. |
| 7,172,601 B2 | 2/2007 | Ben-Nun |
| 7,173,211 B2 | 2/2007 | Coccio et al. |
| 7,202,450 B2 | 4/2007 | Barber et al. |
| 7,527,624 B2 | 5/2009 | Dubnack et al. |
| 7,585,295 B2 | 9/2009 | Ben-Nun |
| 7,597,678 B2 | 10/2009 | Brown |
| 2003/0158567 A1 | 8/2003 | Ben-Nun |
| 2004/0092982 A1 | 5/2004 | Sheffer |
| 2004/0106929 A1 | 6/2004 | Masket |
| 2005/0228419 A1 | 10/2005 | El-Mansoury |
| 2006/0100617 A1 | 5/2006 | Boukhny |
| 2006/0195076 A1 | 8/2006 | Blumenkranz et al. |
| 2006/0264990 A1 | 11/2006 | Michelson et al. |
| 2009/0048619 A1 | 2/2009 | Sobel |
| 2009/0216225 A1 | 8/2009 | Ben-Nun |
| 2010/0057069 A1 | 3/2010 | Ben-Nun |
| 2010/0145447 A1 | 6/2010 | Jia et al. |
| 2010/0179544 A1 | 7/2010 | Boukhny et al. |

FOREIGN PATENT DOCUMENTS

| | | |
|---|---|---|
| JP | 2005080360 A | 3/2005 |
| WO | WO00/35392 | 6/2000 |
| WO | WO2006/109290 | 10/2006 |
| WO | WO2006/117772 | 11/2006 |
| WO | WO2009/140414 | 11/2009 |
| WO | WO2009/140414 A1 | 11/2009 |
| WO | WO2009/153550 | 12/2009 |
| WO | WO2010/044988 | 4/2010 |
| WO | WO2010/068662 | 6/2010 |
| WO | WO2010/080859 | 7/2010 |

OTHER PUBLICATIONS

S Zinn and SL Semiatin, Coil Design and Fabrication: Basic Designed Modifications, Heat Treating, Jun. 1988, pp. 32-41.

Written Opinion of the International Preliminary Examining Authority mailed on Mar. 12, 2013.

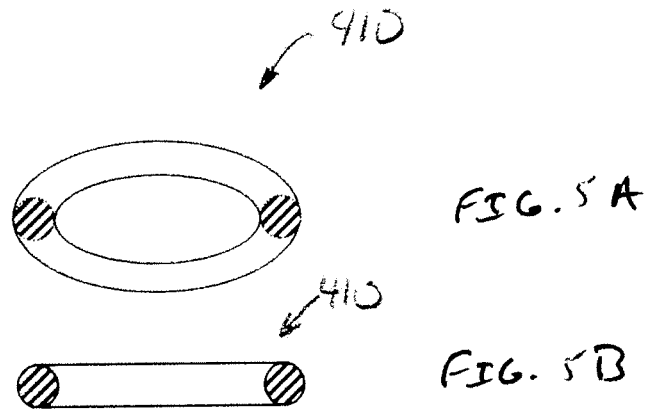
FIG. 5A
FIG. 5B
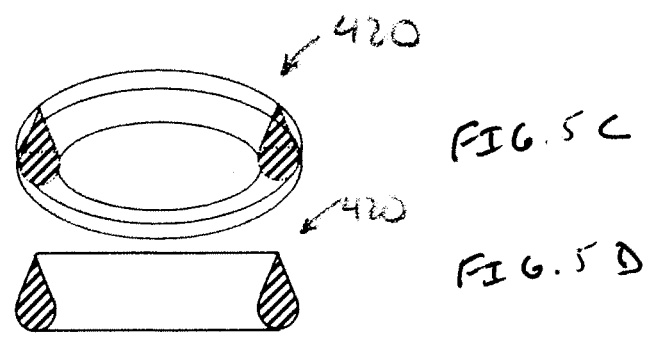
FIG. 5C
FIG. 5D
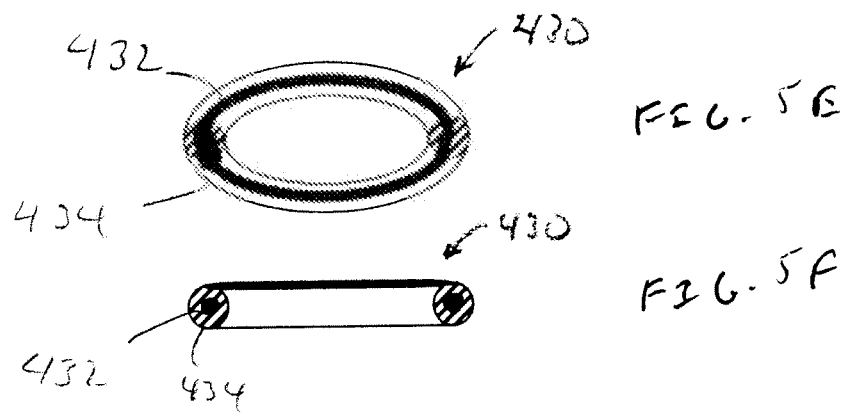
FIG. 5E
FIG. 5F

CAPSULOTOMY DEVICE AND METHOD USING ELECTROMAGNETIC INDUCTION HEATING

FIELD OF INVENTION

The present invention relates to apparatus and methods for forming a capsulotomy, and more particularly apparatus and methods for forming a capsulotomy using electromagnetic induction heating.

BACKGROUND OF THE INVENTION

Surgical procedures for replacing a crystalline lens of a human eye are well known. To practice such procedures, typically an incision is made in a patient's cornea or sclera, and an opening is made in the anterior portion of the capsular bag which surrounds the patient's lens. Such an opening is commonly referred to as a "capsularhexis" (or simply as a "rhexis"); and the process by which the opening is made is commonly referred to as a "capsulotomy." After the opening is made, the eye's lens is removed through the rhexis and a replacement lens (referred to herein as an intraocular lens (or an IOL)) is inserted into the capsular bag through the rhexis.

According to conventional procedures, the incision in the cornea is made with a scalpel, and a pointed stylet or needle is inserted through the incision and is used to rip or tear a generally circular rhexis into the anterior capsular bag.

The use of such a stylet or needle to tear an opening in the anterior capsular bag requires a steady hand and a very high degree of skill. Even when practiced by a skilled surgeon, the potential for incorrectly performing the procedure is substantial.

Forming a rhexis having a larger or smaller diameter than that desired, or inadvertently tearing the capsular bag may prevent the remaining capsular bag from properly retaining an IOL and may result in complications, including infection, damage to other portions of the eye, and potential loss of sight.

As such, although conventional capsulotomy procedures have proven generally suitable for lens replacement surgery, it has deficiencies which may detract substantially from its safety and efficacy. In view of these shortcomings, it is highly desirable to provide a means for reliably and safely forming a rhexis of a desired diameter and shape.

SUMMARY

Aspects of the present invention are directed to a capsulotomy device for use in an eye having a capsular bag, comprising a conductive, primary coil capable of generating magnetic field lines, and a conductive, secondary coil configured to permit insertion through an incision having a diameter of 3 mm or less, and placement on the capsular bag, whereby when the magnetic field lines are projected through the secondary coil a current is generated therein.

In some embodiments, the secondary coil comprises a closed loop. In some embodiments, the secondary coil has a magnetic permeability that is greater than the magnetic permeability of water.

The secondary coil may be configured to form a circular burn trace. The secondary coil may comprise at least one of nitinol, stainless steel and plastic.

In some embodiments, the secondary coil is coupled to a handle. The secondary coil may be disposed in a syringe-type injector. The primary coil may constitute one of a plurality of coils configured to generate the magnetic field lines.

Another aspect of the invention is directed to a method of forming a capsulotomy, comprising locating a conductive coil in contact with a capsular bag of an eye; projecting magnetic field lines through the conductive coil that are projected from a source located outside of the eye to form a burn trace on the capsular bag; and tearing the capsular bag along the burn trace to form a rhexis.

The method may further comprise, prior to the step of locating the conductive coil, folding the coil substantially in half and, while the coil is so folded, inserting the coil into the eye through an incision in the eye.

The term "coil" as used herein refers to a structure comprising at least one substantially complete loop. A coil may comprise multiple complete or partial loops. A loop of a primary coil should be sufficiently complete to form magnetic field lines about an axis extending through a center of the primary coil in a conventional manner for induction heating. A loop of a secondary coil should be sufficiently complete to permit formation of a rhexis upon tearing along a burn trace that is formed when the secondary coil is placed in contact with a capsular bag and operated as described herein below.

The term "diameter" as used herein when referring to a circular shape has its conventional meaning. Said term, when applied to other shapes, refers to any length dimensions of the shape.

BRIEF DESCRIPTION OF THE DRAWINGS

Illustrative, non-limiting embodiments of the present invention will be described by way of example with reference to the accompanying drawings, in which the same reference number is used to designate the same or similar components in different figures, and in which:

FIGS. 5A-5F illustrate three examples of embodiments of secondary coils having different cross-sectional shapes and configurations.

DETAILED DESCRIPTION

Figure 1:
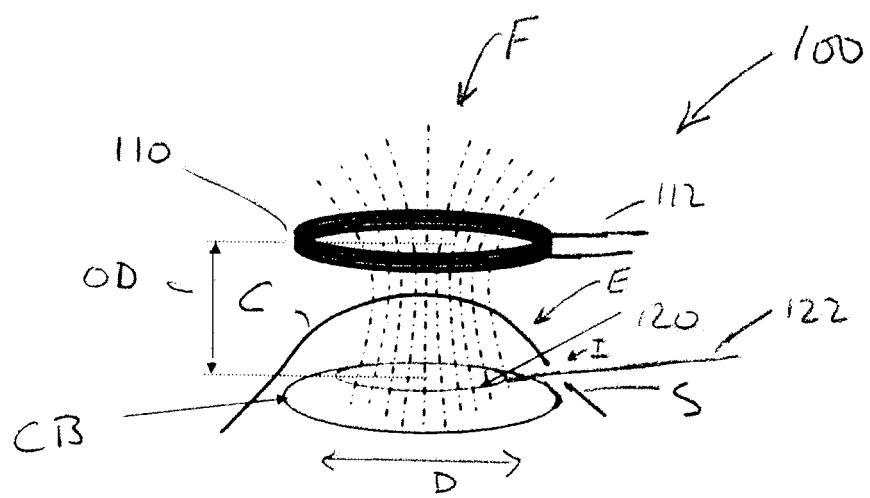
FIG. 1 is a schematic illustration of an example of a device according to aspects of the present invention for performing a capsulotomy using electromagnetic induction heating, the device being positioned in an eye.

FIG. 1 is a schematic illustration of a device 100 for performing a capsulotomy using electromagnetic induction heating, the device being positioned relative to an eye E. The capsulotomy device comprises a conductive primary coil 110 capable of conducting current to generate magnetic field lines F to be projected through a conductive secondary coil 120. The conductive, secondary coil has a diameter D substantially equal to the desired rhexis diameter.

Secondary coil 120 is conductive so as to permit resistive heating in a conventional manner due to movement of electrons (e.g., current) when magnetic field lines are projected through it by primary coil 110. The resulting current may be direct current, alternating current or eddy currents. Due to the inherent resistance of the conductive material comprising the secondary coil, the temperature of the coil will become elevated in response to the current formed therein. In use, the secondary coil is placed in contact with a capsular bag CB of eye E such that the heating causes a partial or complete burn trace on the capsular bag to facilitate removal of the tissue that will be removed to form the rhexis.

Secondary coil 120 is configured to permit insertion through an incision I (in a cornea C or sclera S of the eye) having a diameter of 3 mm or less, and placement on capsular bag CB of eye E. By selecting a suitable material and a suitable cross-section shape, the coil can be folded and/or twisted or otherwise configured to permit entry of the coil through incision I having a diameter of 3 mm or less. An example of a suitable material is nitonol (which is known to have shape memory properties) formed into a generally circular shape having a circular cross-sectional shape with a cross-sectional diameter of a hundred or hundreds of microns (e.g., 0.1 mm). Alternatively, the secondary coil can be made of stainless steel or other metal having a resiliency of shape. In some embodiments, the secondary coil comprises a plastic material having resiliency of shape and having ferromagnetic particles disposed therein.

In some embodiments, the secondary coil forms a closed loop such that after heating of the capsular bag a burn trace is formed which forms a completed line along which tissue can be torn to form the rhexis. In other embodiments, the secondary coil forms less than a complete loop; however the line forms a burn trace that is sufficiently to permit formation of a rhexis upon tearing along a burn trace and a remaining portion of the tissue is torn in a conventional manner (i.e., not along a burn trace). For example, the burn trace may cover greater than 75% of the circumference of a closed shape.

It is typically desirable that the secondary coil have a magnetic permeability that is higher than water to permit selective heating of the closed-loop coil rather than eye tissue, and that the magnetic permeability be relatively high to permit efficient heating of the secondary coil.

Figure 3A:
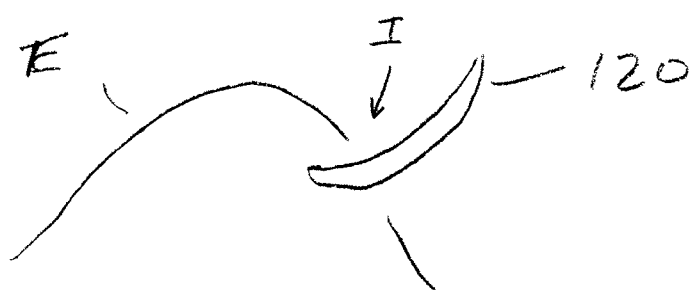
FIGS. 3A and 3B are side and top view illustrations, respectively, of a secondary coil that is folded to facilitate entry into an incision in an eye.
Figure 3B:
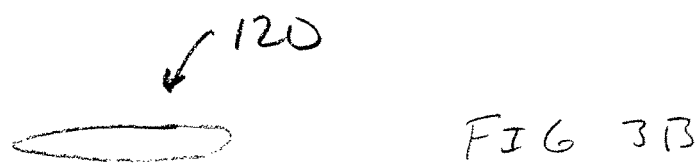
Figure 4A:
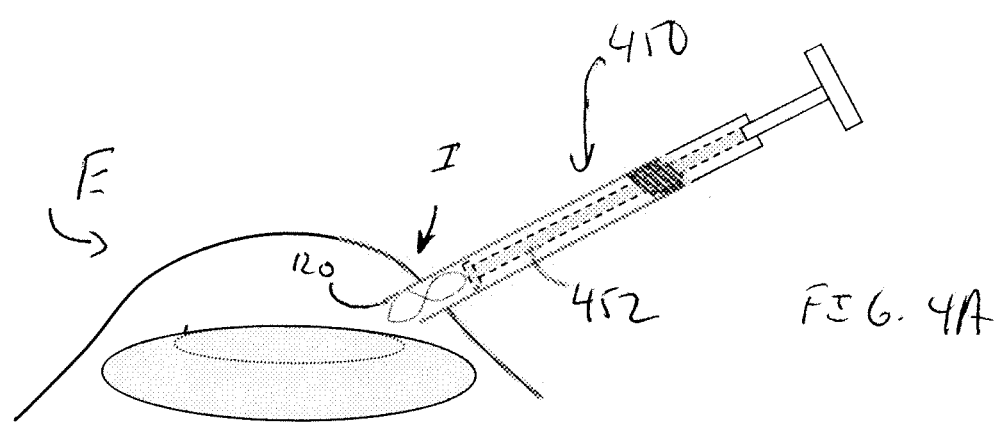
FIGS. 4A and 4B are schematic illustrations of an injector for maintaining and inserting a secondary coil into an eye.
Figure 4B:
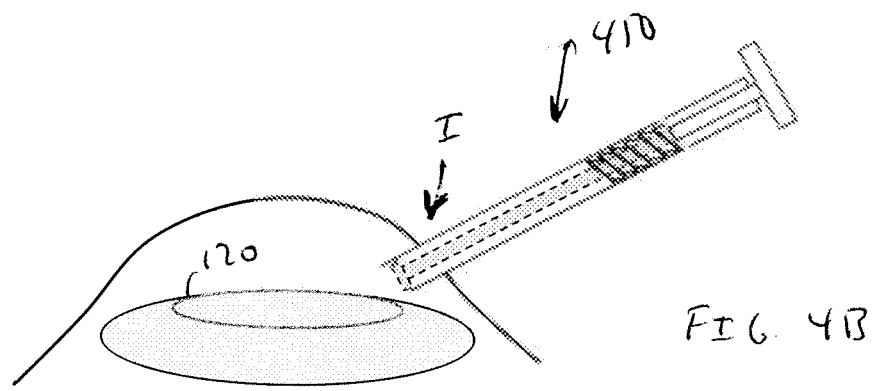

For example, a secondary coil can be substantially folded in half (e.g., see FIGS. 3A and 3B which shows a circular secondary coil folded substantially in half) and slid through the incision and/or can be twisted to facilitate entry into the incision. A suitably configured coil can be delivered though the incision using forceps or tweezers or twisted about an implement (such as a straight pole having a diameter less than about 2.5 mm). The forceps, tweezer or other implement may be used to remove the coil after use. Another possibility to facilitate insertion is a syringe-type device 450, as shown in FIGS. 4A and 4B, that includes a plunger 452 configured and arranged to move the secondary coil into an eye upon actuation of the plunger. Device 450 maintains the secondary coil in a compressed (e.g., folded state) when the secondary coil is within the device and allows the secondary coil to achieve a circular or other shape suitable for forming a rhexis when the secondary coil is expelled from the syringe into the eye by the plunger. In some embodiments, the secondary coil is coupled to the plunger. It will be appreciated that coupling may facilitate removal of the secondary coil by retraction of the plunger.

Conductive, primary coil 110 is capable of generating magnetic field lines that when projected through the conductive secondary coil 120 generate current within the secondary coil. The primary coil produces field lines as a result of current passing the primary coil in a conventional manner. It will be appreciated that the primary coil can be configured to efficiently deliver the field lines through the closed-loop coil when it is positioned on the capsule of an eye. For example, the primary coil can be formed as pancake (i.e., multiple loops of decreasing diameter all formed in a single plane), a conical helix (i.e., multiple loops of decreasing diameter disposed in different planes that are displaced vertically from one another) or a cylinder (i.e., multiple loops of a same diameter disposed in different planes that are displaced vertically from one another) or another known or yet to be developed shape to effectively and efficiently deliver field lines to the secondary coil. It will also be appreciated that a driver is operatively coupled to the primary coil to achieve current through the primary coil in a conventional manner. The driver currents may be direct or alternating currents.

Figure 2:
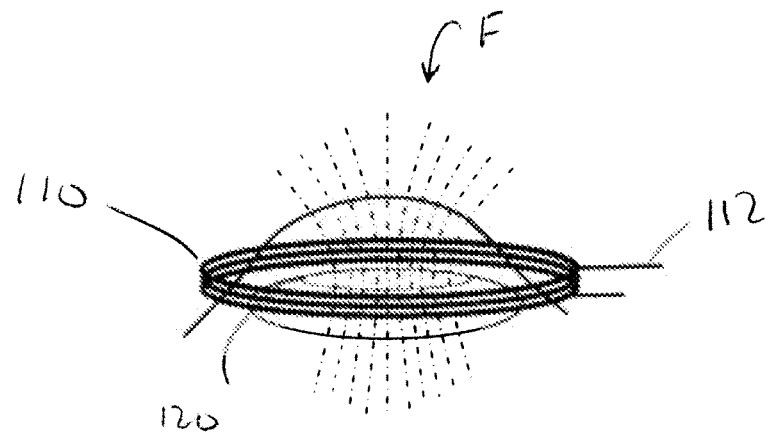
FIG. 2 is a schematic illustration of another example of a device according to aspects of the present invention for performing a capsulotomy using electromagnetic induction heating, the device being positioned in an eye.

In some embodiments, multiple associated or independent primary coils are used to deliver the flux lines to the secondary coil. As one of ordinary skill in the art would understand, such a configuration permits increased flux as well as, with appropriate coordination of currents through the multiple primary coils, the ability to selectively direct the flux lines using appropriate phase relationships between the currents flowing through the primary coils. The coils may be arranged to cause heating by projection over an offset distance OD as shown in FIG. 1 or in a planar configuration as shown in FIG. 2.

Primary coil 110 may be connected to a handle 112 to facilitate handheld positioning of the primary coil by the surgical staff. Alternatively, primary coil 110 may be connected to a stand (not shown) or other piece of surgical equipment to facilitate positioning. Similarly, secondary coil 120 can be connected to a handle 122 or injector as described above.

Typically activation of the primary coil occurs only after the closed-loop coil is located onto the selected surface of the capsular bag CB; however, prior activation is possible. Additionally, typically, the primary coil is deactivated while the closed-loop coil is retracted and removed from the eye.

The surface of the capsular bag that is contacted and heated by the secondary coil may be an interior or an exterior surface of the capsular bag. It will be appreciated that it may be appropriate to provide a surgeon with multiple secondary coils each having a different diameter and/or capable of forming a different predetermined shape S (e.g., circles of different diameters or figures having different shapes). It will also be appreciated that the duration during which current is provided to primary coil, a frequency or frequency pattern of an AC current, and the desired offset distance OD are dependent on cross section of the closed-loop coil, and the surface property of the closed-loop coil as well as the amount of weakening of the capsular bag tissue that is desired.

FIGS. 5A-5F illustrate three examples of embodiments of secondary coils having different cross-sectional shapes. FIGS. 5A and 5B are projection and cut away cross-sectional views, respectively, of a secondary coil 410 having a circular overall shape and a circular cross-sectional shape. FIGS. 5C and 5D are projection and cut away cross-sectional views, respectively, of a secondary coil 420 having a circular overall shape and a modified circular cross-sectional shape where the surface to be placed into contact with the capsular bag is pointed to facilitate localized heating of the capsular bag and to reduce adherence to tissue. FIGS. 5E and 5F are projection view and cut away cross-sectional views, respectively, of a secondary coil 430 having a circular overall shape, a circular cross sectional shape, and having an inner core 432 of a relatively low permeability material and an outer material 434 (e.g., a coating) of a high permeability material.

An aspect of the invention is directed to a method of forming capsulotomy in the following manner. A conductive secondary coil is placed in contact with a capsular bag of an eye. Magnetic field lines are projected through the secondary coil that are projected from a source (e.g., a primary coil) located outside of the eye. Heating of the secondary coil causes formation of a burn trace on the capsular bag. Subsequently, the tissue along the burn trace is torn to form a rhexis. The burn trace may form a closed figure. Alternatively, the burn trace maybe less than closed as described above, where the portion between the ends of the burn trace is torn in the manner of conventional rhexis formation. It will be appreciated that, although the trace is not closed, the precision with which the rhexis is formed is improved due to the presence of the burn trace.

Having thus described the inventive concepts and a number of exemplary embodiments, it will be apparent to those skilled in the art that the invention may be implemented in various ways, and that modifications and improvements will readily occur to such persons. Thus, the embodiments are not intended to be limiting and presented by way of example only. The invention is limited only as required by the following claims and equivalents thereto.

What is claimed is:

1. A capsulotomy device for use in an eye having a capsular bag, comprising:
    a conductive, primary coil capable of generating magnetic field lines; and
    a conductive, secondary coil configured to permit insertion through an incision having a diameter of 3 mm or less, and placement on the capsular bag, the primary coil and secondary coil configured to be independently positionable of one another, relative to the eye,
    the secondary coil adapted to produce resistive heating sufficient to cause a partial or complete burn trace on the capsular bag in response to the magnetic field lines being projected through the secondary coil.

2. The device of claim 1, wherein the secondary coil comprises a closed loop.

3. The device of claim 1, wherein the secondary coil has a magnetic permeability that is greater than the magnetic permeability of water.

4. The device of claim 1, wherein the secondary coil is configured to form a circular burn trace.

5. The device of claim 1, wherein the secondary coil comprises at least one of nitinol, stainless steel and plastic.

6. The device of claim 1, wherein secondary coil is coupled to a handle.

7. The device of claim 1, wherein the secondary coil is disposed in a syringe-type injector.

8. The device of claim 1, wherein the primary coil constitutes one of a plurality of coils each configured to generate the magnetic field lines.

* * * * *